(12) United States Patent
Huang et al.

(10) Patent No.: US 11,965,839 B2
(45) Date of Patent: Apr. 23, 2024

(54) METHOD AND SYSTEM FOR ACQUIRING ELASTIC MODULUS OF ROCK CONTAINING SEDIMENTARY RHYTHMS

(71) Applicant: INSTITUTE OF GEOLOGY AND GEOPHYSICS, CHINESE ACADEMY OF SCIENCES, Beijing (CN)

(72) Inventors: Beixiu Huang, Beijing (CN); Lihui Li, Beijing (CN); Xiao Li, Beijing (CN)

(73) Assignee: INST. OF GEOL. & GEOPHYS., CN ACAD. OF SCIENCES, Beijing (CN)

( * ) Notice: Subject to any disclaimer, the term of this patent is extended or adjusted under 35 U.S.C. 154(b) by 124 days.

(21) Appl. No.: 17/712,927

(22) Filed: Apr. 4, 2022

(65) Prior Publication Data
US 2023/0041637 A1 Feb. 9, 2023

(30) Foreign Application Priority Data
Aug. 6, 2021 (CN) .......................... 202110901612.8

(51) Int. Cl.
*G01N 23/223* (2006.01)
*G01N 33/24* (2006.01)

(52) U.S. Cl.
CPC .......... *G01N 23/223* (2013.01); *G01N 33/24* (2013.01); *G01N 2223/076* (2013.01); *G01N 2223/616* (2013.01)

(58) Field of Classification Search
CPC ................. G01N 23/223; G01N 33/24; G01N 2223/076; G01N 2223/616; G01N 3/08; G01N 2203/0641; G01N 2203/0676
See application file for complete search history.

(56) References Cited

U.S. PATENT DOCUMENTS

| | | | |
|---|---|---|---|
| 2018/0238774 A1* | 8/2018 | Amendt ................. | G01N 33/24 |
| 2020/0149394 A1* | 5/2020 | Hao .......................... | E21B 7/04 |
| 2023/0295482 A1* | 9/2023 | Desouky ................. | C04B 2/02 |
| | | | 166/292 |

OTHER PUBLICATIONS

Venieri et al., Determining elastic properties of organic-rich shales from core, wireline logs and 3-D seismic: A comparative study from the Duvernay play, Alberta, Canada, Sep. 28, 2020, Journal of Natural Gas Science and Engineering vol. 84 pp. 1-12 (Year: 2020).*

* cited by examiner

*Primary Examiner* — Christine S. Kim

(57) ABSTRACT

The present disclosure provides a method and system for acquiring an elastic modulus of a rock containing sedimentary rhythms, including: acquiring a rock sample containing sedimentary rhythms; measuring contents of rock elements in the rock sample at test points with an X-ray fluorescence (XRF) spectrometer, the test points being provided on different rhythms of the rock sample; determining a lithology of the rock sample according to the contents of the rock elements; determining an element-mineral relation equation according to the lithology; determining mineral components of the rock sample with the lithology and the element-mineral relation equation; determining a modulus coefficient of each of minerals according to the mineral components; and determining an elastic modulus of the rock sample according to the mineral components and the modulus coefficient of each of the minerals. The present disclosure can implement nondestructive testing on mechanical properties of rock samples.

4 Claims, 10 Drawing Sheets

METHOD AND SYSTEM FOR ACQUIRING ELASTIC MODULUS OF ROCK CONTAINING SEDIMENTARY RHYTHMS

CROSS REFERENCE TO RELATED APPLICATION

This patent application claims the benefit and priority of Chinese Patent Application No. 202110901612.8, filed on Aug. 6, 2021, the disclosure of which is incorporated by reference herein in its entirety as part of the present application.

TECHNICAL FIELD

The present disclosure relates to the field of testing on mechanical properties of rocks, and in particular, to a method and system for acquiring an elastic modulus of a rock containing sedimentary rhythms.

BACKGROUND ART

The elastic modulus (a ratio of the axial stress to the axial strain when a compressed rock deforms elastically, namely a slope of the linear segment on the stress-strain curve) is a fundamental mechanical parameter for characterizing the capacity of the rock against elastic deformation. The greater the elastic modulus of the rock, the smaller the deformation under a certain stress. For stone cultural relics, the investigation on geomechanical characteristics of the cultural relics is vital for restoration. The elastic modulus in unconventional oil and gas exploitation is an important indicator for measuring brittleness of the rock. It is also directly introduced by many scholars into fracability evaluation systems of unconventional oil and gas reservoirs, to select a sweet spot section in engineering for the most efficient oil and gas exploitation. At present, the elastic modulus of the rock is mainly acquired by direct measurement with standard rock mechanics test in laboratories, or indirect inference based on well-logging data. The former is implemented by preparing standard rock samples each having a diameter of 50 mm and a height of 100 mm or a diameter of 25 mm and a height of 50 mm, performing uniaxial/triaxial compression test with a rock mechanics tester, and calculating the elastic modulus of the rock according to a stress-strain curve obtained from the test. The latter is implemented by performing well drilling on a rock stratum to be analyzed, performing geophysical well logging to obtain well-logging data, and calculating the elastic modulus of the rock in combination with a reliable well-logging data-elastic modulus empirical equation of the research area. Due to strict analytical prerequisites, reliance on standard samples or bases on the well-logging data, the conventional methods are inapplicable to rocks for which the samples cannot be obtained or the samples are limited and cannot meet requirements of the standard mechanics test, and no well-logging data is provided.

The X-ray fluorescence (XRF) as an existing mature technique for analyzing the chemical composition has made a tremendous success in geochemical, industrial and archaeological applications. Over the past few decades, XRF has been developed from a laboratory device to a handheld instrument through which on-site geochemical analysis of the rock can be conducted quickly in field investigation. The portable handheld XRF spectrometer is being widely applied to field geological investigation, material identification on cultural relics, environmental evaluation, and other geochemical fields for its portability, nondestructive testing, economy, high efficiency and so on. As a matter of fact, most rocks in nature are composed of different minerals. The minerals usually have a standard chemical formula, namely the elementary compositions are basically fixed, and the elastic moduli (nano-elastic moduli) of the minerals are also fixed. Hence, for rocks whose elastic moduli cannot be obtained with the conventional methods, the elastic moduli of the rocks can be quickly obtained by introducing the portable XRF spectrometer into the geomechanical field based on an internal element-mineral-rock relation, namely obtaining contents of elements in the rocks and performing a series of transformations, thus providing important field geomechanical data for cultural relic restoration or oil and gas exploitation schemes more timely.

The conventional rock mechanics test is faced with high sampling requirements due to the need for preparing complete cylindrical rock samples with enough sizes, and serious time consumption and high cost due to the need for finely machining the samples and particularly grinding end surfaces of the samples. Due to the destructive testing process, the samples after the test are no longer complete and are inconvenient to conduct other analysis and testing. The geophysical well logging is carried out upon the completion of well drilling, with the long waiting time and high cost.

Generally, the precious stone cultural relics are neither allowable for sampling, nor available for geophysical well logging. For rocks in the deep Earth, available samples are very limited regardless of the quantity or the size due to the large buried depth and hard sampling; and in this case, the standard rock mechanics test cannot be conducted, and the geophysical well logging is also hardly implemented in all drilled wells. Therefore, it is very difficult to measure elastic moduli of surrounding rocks of the stone cultural relics and the rocks in the deep Earth with the conventional methods. There is an urgent need to provide a nondestructive and quick method for acquiring the elastic moduli of these rocks, to quickly determine mechanical properties of the rocks without standard test samples and well-logging data.

SUMMARY

An objective of the present disclosure is to provide a method and system for acquiring an elastic modulus of a rock containing sedimentary rhythms, to implement nondestructive testing on mechanical properties of rock samples.

To implement the foregoing objectives, the present disclosure provides the following solutions:

A method for acquiring an elastic modulus of a rock containing sedimentary rhythms includes:

acquiring a rock sample containing sedimentary rhythms;

measuring contents of rock elements in the rock sample at test points with an XRF spectrometer, the test points being provided on different rhythms of the rock sample;

determining a lithology of the rock sample according to the contents of the rock elements;

determining an element-mineral relation equation according to the lithology;

determining mineral components of the rock sample with the lithology and the element-mineral relation equation;

determining a modulus coefficient of each of minerals according to the mineral components; and determining an elastic modulus of the rock sample according to the mineral components and the modulus coefficient of each of the minerals.

Optionally, the element-mineral relation equation may be calculated by:

$$[W]=[C][T]$$

where, [W] may be a matrix for contents of three-endmember minerals, [T] may be a matrix for contents of characteristic elements, and [C] may be a coefficient matrix.

Optionally, the modulus coefficient of each of the minerals may be calculated by:

$$C_{Ei}=\alpha_i \times E_i$$

where, $C_{Ei}$ may represent a modulus coefficient of a mineral i, $\alpha_i$ may be a weight coefficient of the mineral, and $E_i$ may be a nano-elastic modulus of the mineral i.

Optionally, the elastic modulus may be calculated by:

$$E_I = \sum_{i=1}^{n} C_{Ei} \times W_i$$

where, $E_I$ may represent the elastic modulus of the rock containing sedimentary rhythms, $C_{Ei}$ may represent the modulus coefficient of the mineral i, $W_i$ may be a weight percent of the mineral i, and n may be a number of minerals.

A system for acquiring an elastic modulus of a rock containing sedimentary rhythms includes:

an acquisition module, configured to acquire a rock sample containing sedimentary rhythms;

a measurement module, configured to measure contents of rock elements in the rock sample at test points with an XRF spectrometer, the test points being provided on different rhythms of the rock sample;

a lithology determination module, configured to determine a lithology of the rock sample according to the contents of the rock elements;

an element-mineral relation equation determination module, configured to determine an element-mineral relation equation according to the lithology;

a mineral component determination module, configured to determine mineral components of the rock sample with the lithology and the element-mineral relation equation;

a mineral modulus coefficient determination module, configured to determine a modulus coefficient of each of minerals according to the mineral components; and an elastic modulus determination module, configured to determine an elastic modulus of the rock sample according to the mineral components and the modulus coefficient of each of the minerals.

Optionally, the element-mineral relation equation may be calculated by:

$$[W]=[C][T]$$

where, [W] may be a matrix for contents of three-endmember minerals, [T] may be a matrix for contents of characteristic elements, and [C] may be a coefficient matrix.

Optionally, the modulus coefficient of each of the minerals may be calculated by:

$$C_{Ei}=\alpha_i \times E_i$$

where, $C_{Ei}$ may represent a modulus coefficient of a mineral i, $\alpha_i$ may be a weight coefficient of the mineral, and $E_i$ may be a nano-elastic modulus of the mineral i.

Optionally, the elastic modulus may be calculated by:

$$E_I = \sum_{i=1}^{n} C_{Ei} \times W_i$$

where, $E_I$ may represent the elastic modulus of the rock containing sedimentary rhythms, $C_{Ei}$ may represent the modulus coefficient of the mineral i, $W_i$ may be a weight percent of the mineral i, and n may be a number of minerals.

According to specific embodiments provided by the present disclosure, the present disclosure discloses the following technical effects:

The method and system for acquiring an elastic modulus of a rock containing sedimentary rhythms provided by the present disclosure measure contents of rock elements in the rock sample with the XRF spectrometer, with low requirements on the sample. Moreover, because of nondestructive testing, there is no damage to the sample. The method and system determine the mineral components and the modulus coefficient of each of the minerals through the element-mineral relation equation upon the determination of the contents of the rock elements, and then determine the elastic modulus, so the analysis process is quicker. The sample is unnecessarily machined to further implement the low-cost testing.

BRIEF DESCRIPTION OF THE DRAWINGS

To describe the technical solutions in the embodiments of the present disclosure or in the prior art more clearly, the accompanying drawings required for the embodiments are briefly described below. Apparently, the accompanying drawings in the following description show merely some embodiments of the present disclosure, and a person of ordinary skill in the art may still derive other accompanying drawings from these accompanying drawings without creative efforts.

DETAILED DESCRIPTION OF THE EMBODIMENTS

The technical solutions in the embodiments of the present disclosure are clearly and completely described below with reference to the accompanying drawings. Apparently, the described embodiments are merely a part rather than all of the embodiments of the present disclosure. All other embodiments obtained by the person of ordinary skill in the art on the basis of the embodiments of the present invention without creative efforts shall fall within the protection scope of the present invention.

An objective of the present disclosure is to provide a method and system for acquiring an elastic modulus of a rock containing sedimentary rhythms, to implement nondestructive testing on mechanical properties of rock samples.

To make the above objectives, features, and advantages of the present disclosure clearer and more comprehensible, the present disclosure will be further described in detail below with reference to the accompanying drawings and the specific examples.

Figure 1:
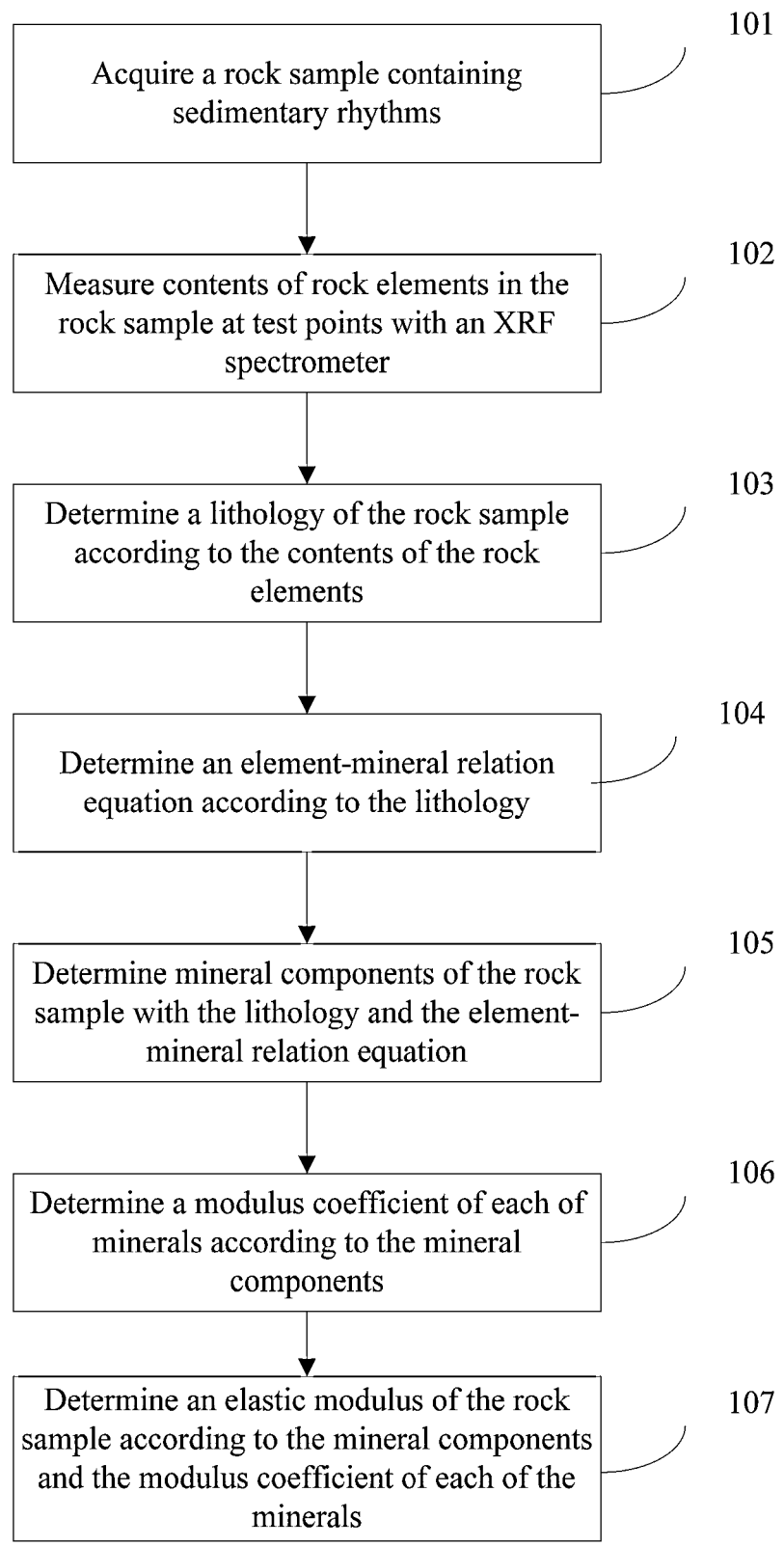
FIG. 1 illustrates a flow chart of a method for acquiring an elastic modulus of a rock containing sedimentary rhythms according to the present disclosure.

As shown in FIG. 1, the present disclosure provides a method for acquiring an elastic modulus of a rock containing sedimentary rhythms, including:

Step 101: Acquire a rock sample containing sedimentary rhythms.

Step 102: Measure contents of rock elements in the rock sample at test points with an XRF spectrometer, the test points being provided on different rhythms of the rock sample.

Step 103: Determine a lithology of the rock sample according to the contents of the rock elements.

Step 104: Determine an element-mineral relation equation according to the lithology.

Step 105: Determine mineral components of the rock sample with the lithology and the element-mineral relation equation.

Step 106: Determine a modulus coefficient of each of minerals according to the mineral components.

Step 107: Determine an elastic modulus of the rock sample according to the mineral components and the modulus coefficient of each of the minerals.

In actual applications, the element-mineral relation equation is calculated by:

$$[W]=[C][T]$$

where, [W] is a matrix for contents of three-endmember minerals, [T] is a matrix for contents of characteristic elements, and [C] is a coefficient matrix.

In actual applications, a modulus coefficient of each of the minerals are calculated by:

$$C_{Ei}=\alpha_i \times E_i$$

where, $C_{Ei}$ represents a modulus coefficient of a mineral i, $\alpha_i$ is a weight coefficient of the mineral, and $E_i$ is a nano-elastic modulus of the mineral i.

In actual applications, the elastic modulus is calculated by:

$$E_l = \sum_{i=1}^{n} C_{Ei} \times W_i$$

where, $E_l$ represents the elastic modulus of the rock containing sedimentary rhythms, $C_{Ei}$ represents the modulus coefficient of the mineral i, $W_i$ is a weight percent of the mineral i, and n is a number of minerals.

Figure 2:
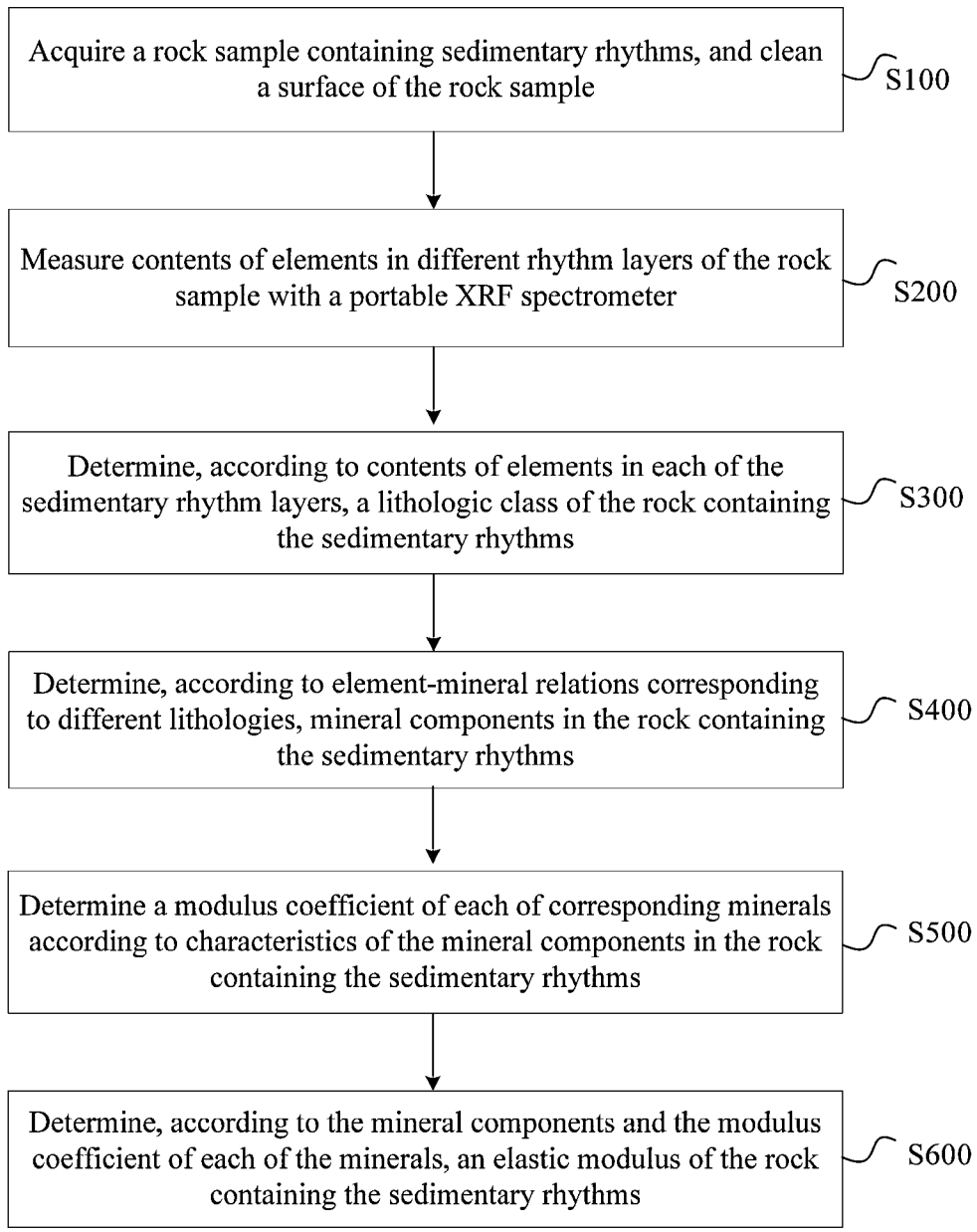
FIG. 2 illustrates a more specific flow chart of a method for acquiring an elastic modulus of a rock containing sedimentary rhythms according to the present disclosure.

As shown in FIG. 2, the present disclosure further provides a more specific method for acquiring an elastic modulus of a rock containing sedimentary rhythms. With the shale core of the drilled XK01 well for scientific research in Xishui area of Northern Guizhou as an example, descriptions will be made below to how the elastic modulus of the shale is obtained with the method. The XK01 well has a depth of 156.35 m, with the target stratum being the Upper Ordovician Wufeng-Lower Silurian Longmaxi shale at about 450 million years from now. Through on-site gas content measurement, there is a section having a thickness of about 20-30 m and a high gas content of about 2.2-3.9 m³ per cubic meter of rock at the bottom of the Wufeng-Longmaxi shale. Upon well completion, ignition test is performed on the wellhead and the desirable effect is achieved, indicating that the area has the enormous potential to explore and develop the shale gas.

FIG. 2 illustrates a flow chart for acquiring the elastic modulus of the shale. Herein, the key step is to determine mineral components based on element scanning data, and acquire the elastic modulus of the shale in combination with a modulus coefficient of each of minerals. The specific process is as follows:

Step 100: Acquire a rock sample containing sedimentary rhythms, and clean a surface of the rock sample.

The Wufeng-Longmaxi shale sample at the depth of 10.94-142.65 m in the XK01 well is acquired, the surface of the sample is cleaned, and sedimentary rhythms are labeled according to a certain distance. The shale sample may be a complete core, a broken rock block or even a rock debris. The distance between two adjacent test points is determined by a test depth. It is generally 0.1-1 m, preferably 0.5 m.

Step 200: Measure contents of elements in different rhythm layers of the rock sample with a portable XRF spectrometer.

Figure 3A:
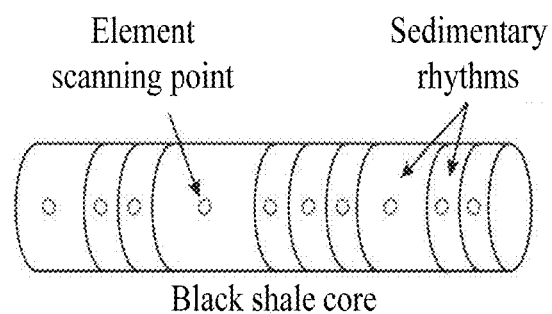
FIG. 3A schematically illustrates a rock containing sedimentary rhythms.
Figure 3B:
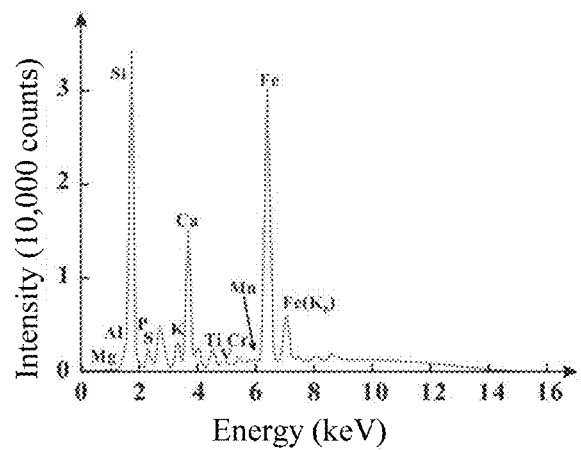
FIG. 3B illustrates element scanning of an XRF spectrometer according to the present disclosure.

Contents of shale elements at labeled places are measured with the portable handheld XRF spectrometer. At the drilling site, the XRF spectrometer can be held by hands or cooperatively used with a tripod. The labeled places are the test points, as shown in FIG. 3A. FIG. 3A illustrates the rock containing the sedimentary rhythms, in which the dot in the middle represents the element scanning point, and contents of more than 30 elements between Mg and U, mainly including Si, Al, K, Ca, Mg, P, S, Fe, V, Ti, U, Th, Ba, Zr, Mn and Sr, can be obtained. The scanning result is as shown in FIG. 3B. FIG. 3B schematically illustrates an XRF spectrum of the rock containing sedimentary rhythms.

Step 300: Determine, according to contents of elements in each of the sedimentary rhythm layers, a lithologic class of the rock containing sedimentary rhythms.

Figure 4A:
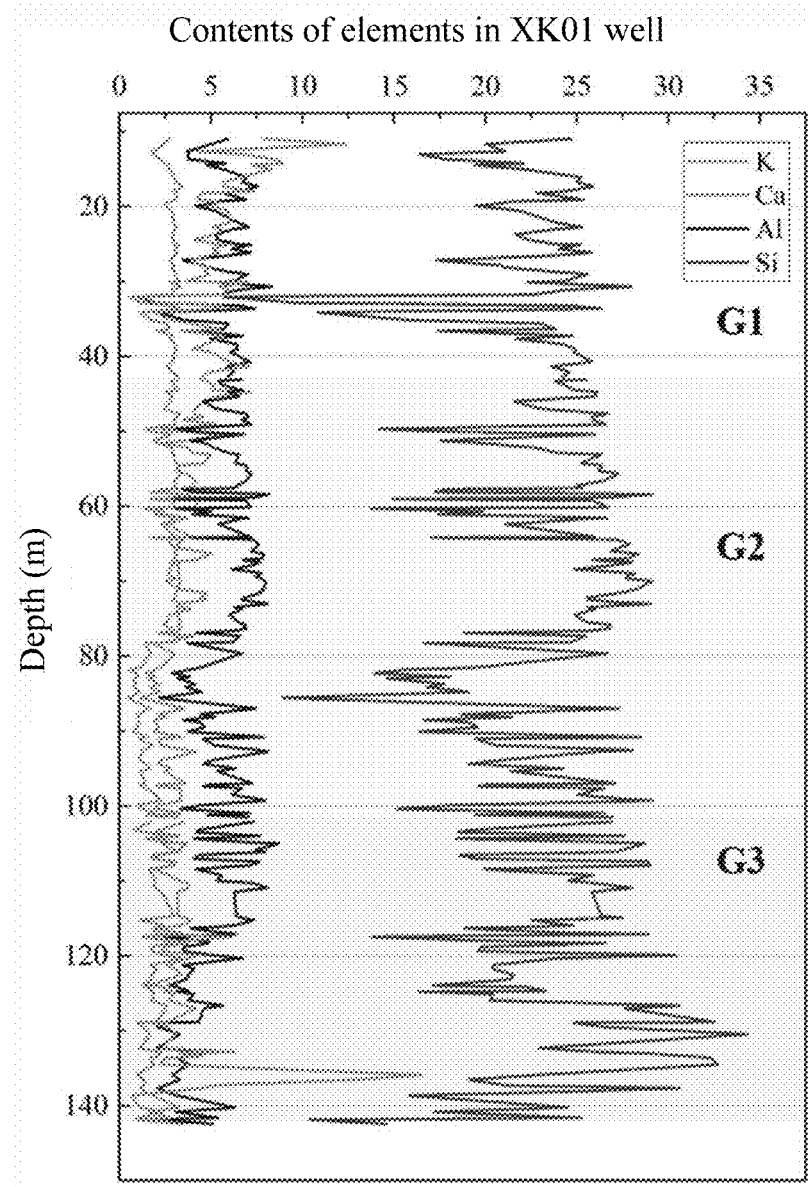
FIG. 4A illustrates an element content-depth curve obtained by element scanning of an XRF spectrometer on a rock containing sedimentary rhythms.
Figure 4B:
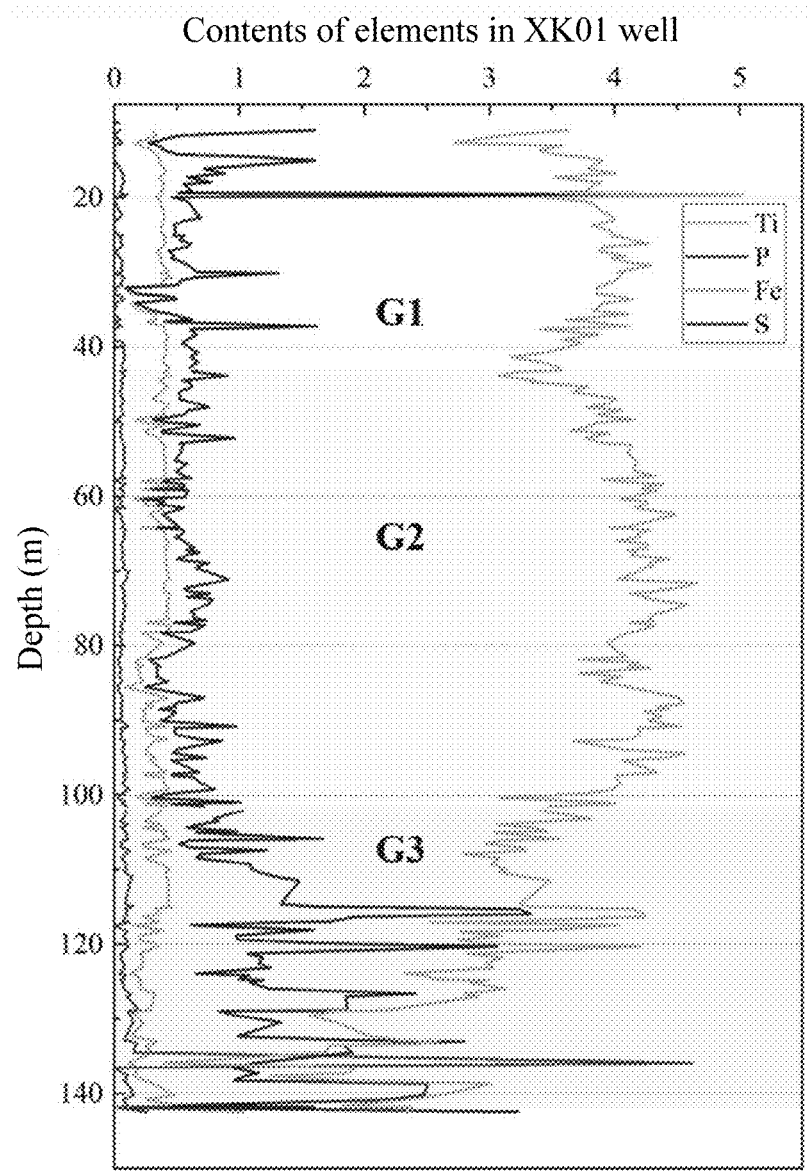
FIG. 4B shows a medium-content element-depth curve.
Figure 4C:
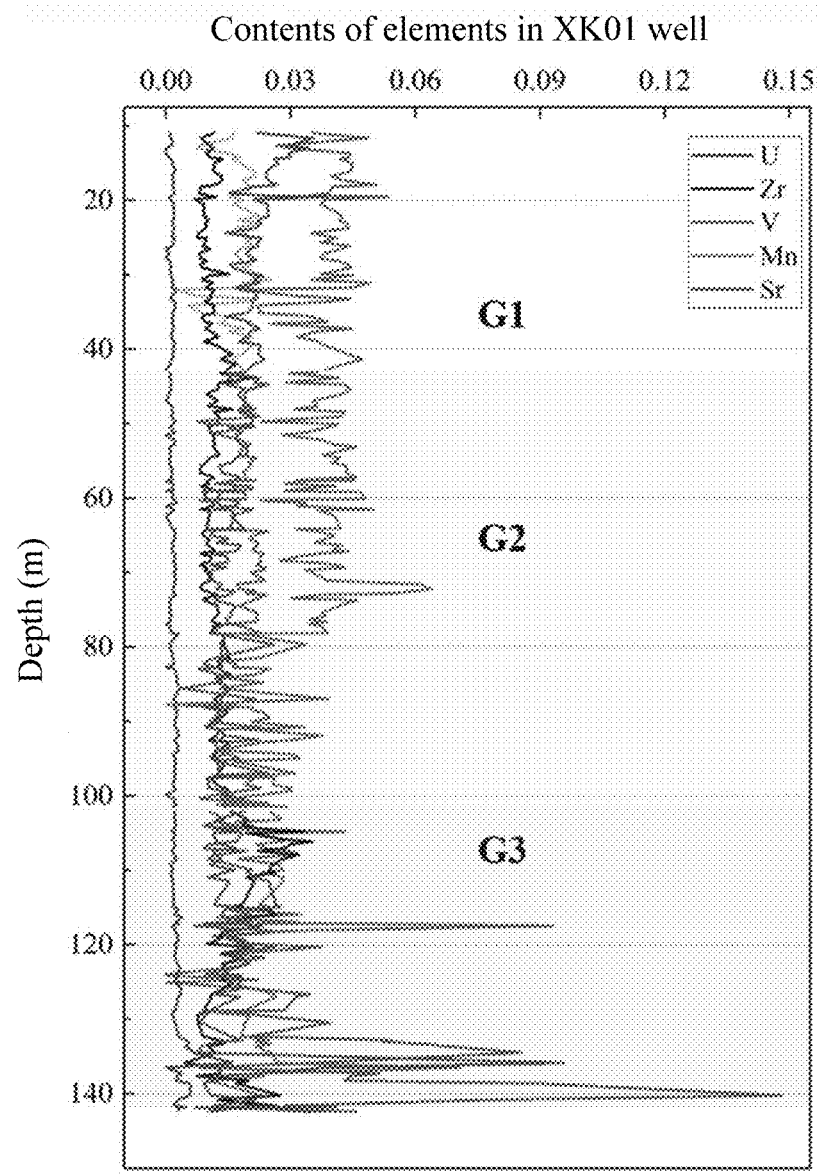
FIG. 4C shows a low-content element-depth curve.

The lithology of the rock containing sedimentary rhythms is subdivided according to contents of representative elements (such as Ca, Fe, Al, S and U) in the rock containing sedimentary rhythms in Step 200. The general lithology of the rock is determined approximately according to the color, structure and particle size of the rock containing sedimentary rhythms (for example, the rock is the shale, sandstone or conglomerate). The specific lithology of the rock is further subdivided in combination with the contents of characteristic elements (namely the representative elements such as Ca, Fe, Al, S and U) in the rock (for example, the rock is the calcareous, sandy or organic-rich shale, or the ferruginous shale). The shale core of the XK01 well in the embodiment is determined as the calcareous shale if the content of the Ca element is obviously higher, as the sandy shale if the contents of the Fe and Al elements are higher, and as the organic-rich shale if the contents of the S and U elements are higher. From top to bottom, the core of the XK01 well includes the calcareous shale (G1 at the corresponding depth of 10.94-42.74 m), the sandy shale (G2 at the corresponding depth of 43.08-101.46 m), and the organic-rich shale (G3 at the corresponding depth of 102.05-142.65 m), with the corresponding element content-depth curve as shown in FIG. 4A-C. FIG. 4A shows a high-content element-depth curve, FIG. 4B shows a medium-content element-depth curve, and FIG. 4C shows a low-content element-depth curve. G1-G3 respectively represent three different lithologies of rocks containing sedimentary rhythms, namely the calcareous shale, the sandy shale and the organic-rich shale.

Step 400: Select corresponding element-mineral relation equations according to different lithologies to determine mineral components of the rock containing sedimentary rhythms.

Figure 5:
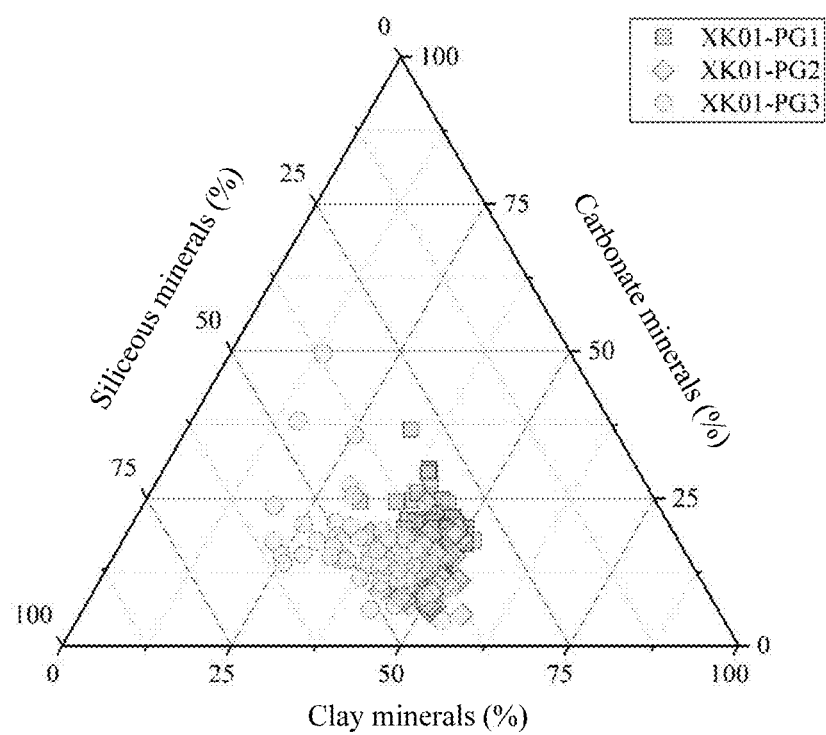
FIG. 5 illustrates a distribution of three-endmember minerals in a rock containing sedimentary rhythms.

Element-mineral relation equation libraries for different lithologies have been established in preliminary study. According to the lithology of the rock containing sedimentary rhythms, the element-mineral relation equation matching with the lithology of the rock to be analyzed is selected from the element-mineral relation equation libraries for the different lithologies. For example, for the calcareous shale, the element-mineral relation equation corresponding to the calcareous shale is selected from the equation libraries; and for the sandy shale, the element-mineral relation equation corresponding to the sandy shale is selected from the equation libraries. The mineral components of the rock containing sedimentary rhythms, as shown in FIG. 5, are obtained according to the corresponding element-mineral relation equation, namely Equation (1). The relation between the mineral components and the contents of the characteristic elements can be expressed as follows:

$$[W]=[C][T] \quad (1)$$

where, [W] is a matrix for contents of three-endmember minerals, including siliceous minerals (quartz, feldspar and pyrite), carbonate minerals (calcite, dolomite and ankerite) and clay minerals (kaolinite, illite, montmorillonite and chlorite), [T] is a matrix for contents of characteristic elements, including high-content elements (K, Ca, Al and Si), medium-content elements (P, Ti, S and Fe) and low-content elements (U, Zr, V, Mn and Sr), both the matrix for the minerals and the matrix for the elements having a unit of %, and [C] is a coefficient matrix and is dimensionless.

With the calcareous shale (G1) as an example, the corresponding specific matrix is as follows:

$$\begin{bmatrix} W_{11} \\ W_{21} \\ W_{31} \end{bmatrix} = \begin{bmatrix} C_{11} & \cdots & C_{1m} \\ C_{21} & \ddots & C_{2m} \\ C_{31} & \cdots & C_{3m} \end{bmatrix} \begin{bmatrix} T_{11} \\ \vdots \\ T_{m1} \end{bmatrix} \quad (2)$$

where, $W_{i1}$ represents a content of a three-endmember mineral i in G1, i=1-3, respectively representing the siliceous minerals, the carbonate minerals and the clay minerals, $T_{m1}$ represents a content of a characteristic element m in G1, m=1-7, respectively representing Sr, Fe, S, K, Ca, Al and a constant 1, and $C_{im}$ is a coefficient for the corresponding characteristic element m of the mineral i, with the following specific values:

$C_{11}$=−332.98, $C_{12}$=10.60, $C_{13}$=−3.20, $C_{14}$=0, $C_{15}$=0, $C_{16}$=0, and $C_{17}$=13.97.

$C_{21}$=265.03, $C_{22}$=0, $C_{23}$=0, $C_{24}$=−3.56, $C_{25}$=1.56, $C_{26}$=0, and $C_{27}$=16.74.

$C_{31}$=0, $C_{32}$=−11.41, $C_{33}$=3.98, $C_{34}$=0, $C_{35}$=−1.49, $C_{26}$=1.22, and $C_{37}$=75.82.

Step 500: Determine a modulus coefficient of each of corresponding minerals according to characteristics of the mineral components in the rock containing sedimentary rhythms.

The modulus coefficient of each of the minerals is determined according to the characteristics of the mineral components in the rock containing sedimentary rhythms in Step 400, in combination with a nano-elastic modulus of each of the minerals and a weight of each of the minerals. The nano-elastic modulus of each of the minerals is determined according to the Rock Physics Handbook or references. The weight of each of the minerals can be determined with reference to a regression model for an elastic modulus of a standard sedimentary rhythm stratum and contents of corresponding minerals.

The relation among the modulus coefficient of each of the minerals, the nano-elastic modulus of each of the minerals and the weight of each of the minerals can be expressed as follows:

$$C_{Ei}=\alpha_i \times E_i \quad (3)$$

where, $C_{Ei}$ represents a modulus coefficient of a mineral i, $\alpha_i$ is a weight coefficient of the mineral, and $E_i$ is a nano-elastic modulus (GPa) of the mineral i.

Figure 6:
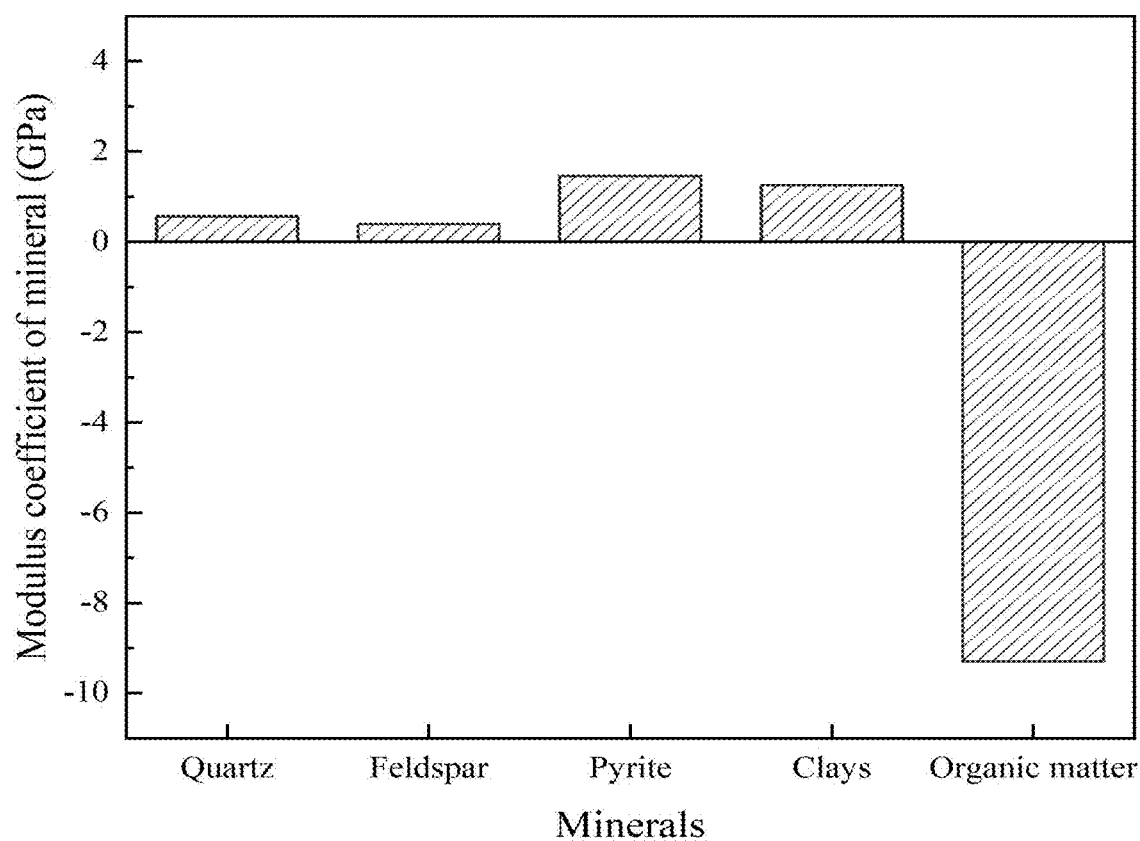
FIG. 6 schematically illustrates a distribution of modulus coefficients of minerals in a rock containing sedimentary rhythms.

In the embodiment, i=1-5 (i=1, representing the quartz; i=2, representing the feldspar; i=3, representing the pyrite; i=4, representing the clay mineral; and i=5, representing the organic mineral), and the modulus coefficients of the corresponding minerals are as shown in FIG. 6.

Step 600: Determine, according to the mineral components and the modulus coefficient of each of the minerals, an elastic modulus of the rock containing sedimentary rhythms. Based on the close element-mineral-rock relation, the present disclosure can quickly obtain the elastic modulus after obtaining the contents of the elements in the rock containing sedimentary rhythms. The elemental analysis in the method is the nondestructive testing with a fast-testing speed, and thus is particularly suitable for rocks without standard test samples and well-logging data.

According to the characteristics of the mineral components in the rock containing sedimentary rhythms and the modulus coefficient of each of the minerals, the elastic modulus of the rock containing sedimentary rhythms is determined. The relation among the elastic modulus of the rock containing sedimentary rhythms, the weight coefficient of each of the minerals and the content of each of the minerals can be expressed as follows:

$$E_l = \sum_{i=1}^{n} C_{Ei} \times W_i \quad (4)$$

where, $E_l$ represents the elastic modulus (GPa) of the rock containing sedimentary rhythms, $W_i$ is a weight percent (wt. %) of the mineral i, and n is a number of minerals.

Figure 7:
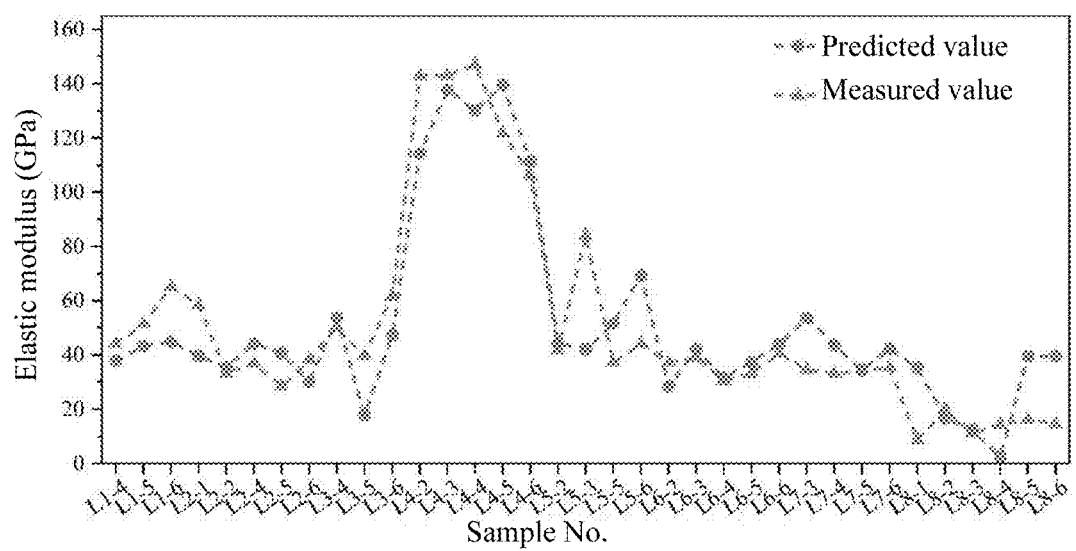
FIG. 7 illustrates a comparison between a predicted value and a measured value for an elastic modulus of a rock containing sedimentary rhythms.

According to the above method, predicted values of elastic moduli for a part of rocks are obtained based on characteristics of mineral components in rocks containing sedimentary rhythms, as shown in FIG. 7. The predicted values are basically consistent with measured values of the elastic moduli obtained by the rock mechanics test. Therefore, the method is feasible, and can be directly applied to the on-site analysis for mechanical characteristics of the rocks.

Figure 8:
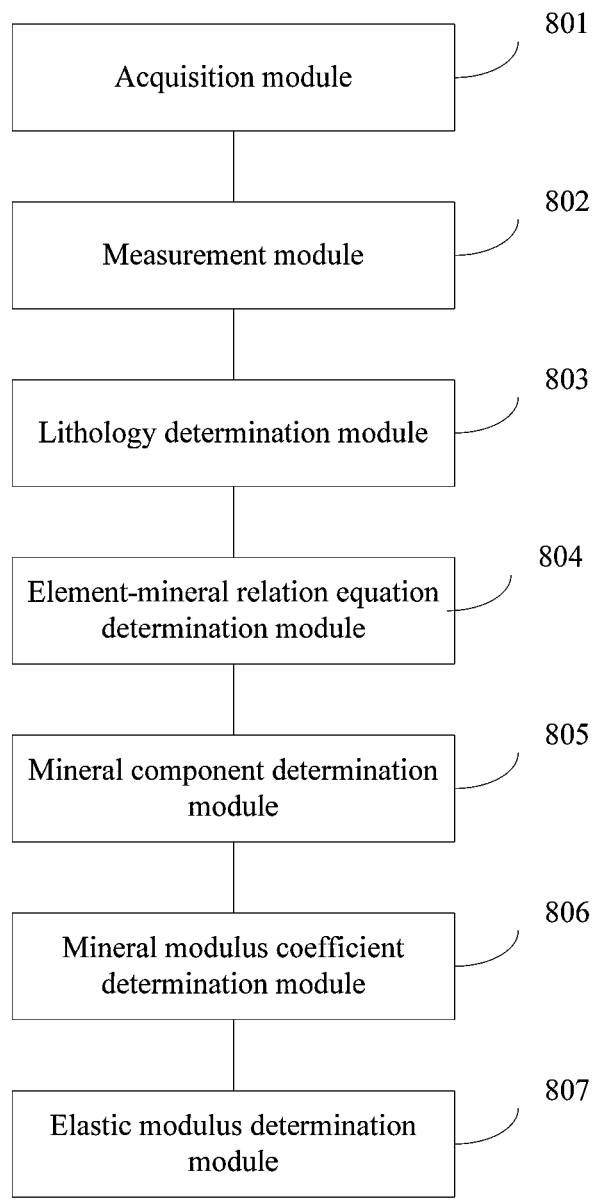
FIG. 8 systematically illustrates a system for acquiring an elastic modulus of a rock containing sedimentary rhythms.

As shown in FIG. 8, the present disclosure provides a system for acquiring an elastic modulus of a rock containing sedimentary rhythms, including:

an acquisition module 801, configured to acquire a rock sample containing sedimentary rhythms;

a measurement module 802, configured to measure contents of rock elements in the rock sample at test points with an XRF spectrometer, the test points being provided on different rhythms of the rock sample;

a lithology determination module 803, configured to determine a lithology of the rock sample according to the contents of the rock elements;

an element-mineral relation equation determination module 804, configured to determine an element-mineral relation equation according to the lithology;

a mineral component determination module 805, configured to determine mineral components of the rock sample with the lithology and the element-mineral relation equation;

a mineral modulus coefficient determination module 806, configured to determine a modulus coefficient of each of minerals according to the mineral components; and an elastic modulus determination module 807, configured to determine an elastic modulus of the rock sample according to the mineral components and the modulus coefficient of each of the minerals.

In actual applications, the element-mineral relation equation is calculated by:

$$[W]=[C][T]$$

where, [W] may be a matrix for contents of three-endmember minerals, [T] may be a matrix for contents of characteristic elements, and [C] may be a coefficient matrix.

In actual applications, a modulus coefficient of each of the minerals are calculated by:

$$C_{Ei}=\alpha_i \times E_i$$

where, $C_{Ei}$ may represent a modulus coefficient of a mineral i, $\alpha_i$ may be a weight coefficient of the mineral, and $E_i$ may be a nano-elastic modulus of the mineral i.

In actual applications, the elastic modulus is calculated by:

$$E_l = \sum_{i=1}^{n} C_{Ei} \times W_i$$

where, $E_l$ may represent the elastic modulus of the rock containing sedimentary rhythms, $C_{Ei}$ may represent the modulus coefficient of the mineral i, $W_i$ may be a weight percent of the mineral i, and n may be a number of minerals.

The method and system for acquiring an elastic modulus of a rock containing sedimentary rhythms provided by the present disclosure achieve the following advantages:

1. The present disclosure uses a portable handheld XRF spectrometer to perform element scanning on the surface of the rock containing sedimentary rhythms, and divides the lithology according to contents of characteristic elements. The requirements on the sample are low, there is no need to specially prepare the sample, and the sample can be the complete rock mass, core plug, rock block or rock debris. The element scanning in the present disclosure is nondestructive testing without any damage to the sample, and thus is particularly applied to rocks for which samples cannot be obtained or rare samples are obtained, such as the stone cultural relics or the rocks in the deep Earth. The scanned sample can further be used for other analysis and testing.

2. The present disclosure determines the lithology of the rock containing sedimentary rhythms, selects the corresponding element-mineral relation model according to the lithology, and determines the mineral composition according to the contents of the characteristic elements; and determines modulus coefficients of corresponding minerals according to the mineral composition of the rock containing sedimentary rhythms in combination with the nano-elastic modulus of each of the minerals and the weight of each of the minerals, and obtains the elastic modulus of the rock containing sedimentary rhythms. The present disclosure can divide the lithology and determine the mineral composition upon obtaining the contents of the elements in the rock containing sedimentary rhythms, and obtains the elastic modulus in combination with the modulus coefficient of each of the minerals. The whole analytical process is quick and can be accomplished with 5 min. There is no need to specially machine the sample, so the cost is low. Moreover, the present disclosure is not restricted by the site and can be conducted in the field geological investigation site, thereby providing important geomechanical parameters for cultural relic restoration or oil and gas exploitation schemes timely.

Each embodiment of the present specification is described in a progressive manner, each embodiment focuses on the difference from other embodiments, and the same and similar parts between the embodiments may refer to each other. Since the system disclosed in an embodiment corresponds to the method disclosed in another embodiment, the description is relatively simple, and reference can be made to the method description.

Specific examples are used herein to explain the principles and embodiments of the present disclosure. The foregoing description of the embodiments is merely intended to help understand the method of the present disclosure and its core ideas; besides, various modifications may be made by the person of ordinary skill in the art to specific embodiments and the scope of application in accordance with the ideas of the present disclosure. In conclusion, the content of the present description shall not be construed as limitations to the present disclosure.

What is claimed is:

1. A method for acquiring an elastic modulus of a rock containing sedimentary rhythms, comprising:

acquiring a rock sample containing sedimentary rhythms;

measuring contents of rock elements in the rock sample at test points with an X-ray fluorescence (XRF) spectrometer, the test points being provided on different rhythms of the rock sample;

determining a lithology of the rock sample according to the contents of the rock elements;

determining an element-mineral relation equation according to the lithology;

determining mineral components of the rock sample with the lithology and the element-mineral relation equation;

determining a modulus coefficient of each of minerals according to the mineral components; and determining an elastic modulus of the rock sample according to the mineral components and the modulus coefficient of each of the minerals.

2. The method for acquiring an elastic modulus of a rock containing sedimentary rhythms according to claim 1, wherein the element-mineral relation equation is calculated by:

$$[W]=[C][T]$$

wherein, [W] is a matrix for contents of three-endmember minerals, [T] is a matrix for contents of characteristic elements, and [C] is a coefficient matrix.

3. The method for acquiring an elastic modulus of a rock containing sedimentary rhythms according to claim 1, wherein the modulus coefficient of each of the minerals is calculated by:

$$C_{Ei} = \alpha_i \times E_i$$

wherein, $C_{Ei}$ represents a modulus coefficient of a mineral i, $\alpha_i$ is a weight coefficient of the mineral, and $E_i$ is a nano-elastic modulus of the mineral i.

4. The method for acquiring an elastic modulus of a rock containing sedimentary rhythms according to claim 1, wherein the elastic modulus is calculated by:

$$E_l = \sum_{i=1}^{n} C_{Ei} \times W_i$$

wherein, $E_l$ represents the elastic modulus of the rock containing sedimentary rhythms, $C_{Ei}$ represents the modulus coefficient of the mineral i, $W_i$ is a weight percent of the mineral i, and n is a number of minerals.

* * * * *